United States Patent
Stawski et al.

(10) Patent No.: US 8,557,323 B2
(45) Date of Patent: *Oct. 15, 2013

(54) BREATH FRESHENING CONFECTIONERY PRODUCTS AND METHODS OF MAKING AND USING SAME

(71) Applicant: WM. Wrigley Jr. Company, Chicago, IL (US)

(72) Inventors: Barbara Z. Stawski, Forrest Park, IL (US); Thomas M. Mindak, Itasca, IL (US); Philip M. Soukup, Lake Mary, FL (US); Gordon N. McGrew, Chicago, IL (US); James C. Clark, St. Louis, MO (US); Michael S. Haas, Naperville, IL (US); Miguel Perez, Chicago, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/678,244

(22) Filed: Nov. 15, 2012

(65) Prior Publication Data

US 2013/0071454 A1    Mar. 21, 2013

Related U.S. Application Data

(63) Continuation of application No. 11/550,940, filed on Oct. 19, 2006, which is a continuation of application No. PCT/US2005/013544, filed on Apr. 20, 2005.

(60) Provisional application No. 60/650,785, filed on Feb. 7, 2005, provisional application No. 60/650,786, filed on Feb. 7, 2005, provisional application No. 60/564,053, filed on Apr. 20, 2004.

(51) Int. Cl.
    *A23G 3/00*    (2006.01)

(52) U.S. Cl.
    USPC .......................................... 426/660; 424/440

(58) Field of Classification Search
    USPC .......................................................... 426/660
    See application file for complete search history.

(56) References Cited

U.S. PATENT DOCUMENTS

| 2,106,097 A | 1/1938 | Homan |
| 2,312,381 A | 3/1943 | Bickenheuser |

(Continued)

FOREIGN PATENT DOCUMENTS

| DE | 102 61 700 A1 | 7/2004 |
| EP | 0 481 940 A | 4/1992 |

(Continued)

OTHER PUBLICATIONS

"The Mouth—Human Anatomy". Retrieved on Jan. 16, 2013 from www.theodora.com/anatomy/the mouth. pp. 1-23.*

(Continued)

Primary Examiner — D. Lawrence Tarazano
Assistant Examiner — Jenna A Watts
(74) Attorney, Agent, or Firm — Steven P. Shurtz; Brinks Hofer Gilson & Lione

(57) ABSTRACT

A confectionery product comprises a first side and a second side generally opposite to the first side; the second side comprising an abrasive surface that is suitable for scrubbing the top surface of a tongue within the oral cavity. in preferred embodiments the first side is smooth and domed shaped. The abrasive surface may be generally convex and be provided by 1) a formed, uneven surface, 2) by including abrasive particles in the composition making up the second surface, or 3) a combination of a formed, uneven surface and abrasive particles. The confectionery product is preferably a hard confectionery, such as a pressed tablet. Preferred pressed tablets are made from a compressible composition and have at least one abrasive surface suitable for cleaning the surface of a human tongue in an oral cavity.

24 Claims, 9 Drawing Sheets

(56) References Cited

U.S. PATENT DOCUMENTS

| | | | |
|---|---|---|---|
| 2,987,445 A | 6/1961 | Levesque |
| 3,048,526 A | 8/1962 | Boswell |
| 4,112,066 A | 9/1978 | Hussein |
| 4,263,328 A | 4/1981 | Parada et al. |
| D285,490 S | 9/1986 | Tovey |
| 4,692,339 A | 9/1987 | Stetson et al. |
| 4,804,548 A | 2/1989 | Sharma et al. |
| 4,847,090 A | 7/1989 | Della Posta et al. |
| 5,462,760 A | 10/1995 | Serpelloni et al. |
| 5,786,017 A | 7/1998 | Blake et al. |
| 6,004,334 A | 12/1999 | Mythen |
| 6,030,605 A | 2/2000 | D'Ameila et al. |
| 6,083,235 A | 7/2000 | Wagner |
| 6,083,527 A | 7/2000 | Thistle |
| 6,161,260 A | 12/2000 | Flewitt |
| 6,280,762 B1 | 8/2001 | Bealin-Kelly et al. |
| D464,786 S | 10/2002 | Stanton |
| 6,582,731 B1 | 6/2003 | Kaufmann |
| D477,866 S | 7/2003 | Dubois et al. |
| 6,607,771 B2 | 8/2003 | Benczedi et al. |
| D509,942 S | 9/2005 | Connolly et al. |
| 7,063,858 B2 | 6/2006 | Saniez et al. |
| 7,090,687 B1 | 8/2006 | Gwen |
| 2002/0132000 A1 | 9/2002 | Saniez et al. |
| 2002/0198552 A1 | 12/2002 | Yavitz |
| 2003/0007997 A1 | 1/2003 | Lawlor |
| 2003/0008062 A1* | 1/2003 | Day et al. ............... 426/660 |
| 2003/0152668 A1 | 8/2003 | Griffin |
| 2003/0163149 A1 | 8/2003 | Heisinger |
| 2003/0224090 A1 | 12/2003 | Pearce et al. |
| 2004/0156794 A1 | 8/2004 | Barkalow et al. |
| 2006/0193909 A1 | 8/2006 | Stawski et al. |
| 2007/0166430 A1 | 7/2007 | Stawski et al. |
| 2007/0181185 A1 | 8/2007 | Clark |

FOREIGN PATENT DOCUMENTS

| | | |
|---|---|---|
| EP | 0 267 160 A | 5/1998 |
| EP | 1 214 892 B1 | 6/2002 |
| EP | 1 222 860 A2 | 7/2002 |
| JP | 1997-25221 | 1/1997 |
| WO | WO 91/07100 A1 | 11/1990 |
| WO | WO 01/35764 A1 | 5/2001 |
| WO | WO 2005/102066 A2 | 11/2005 |

OTHER PUBLICATIONS

"Ellipse". Retrieved online from mathopenreference.com on May 7, 2013. pp. 1-2.*

Firmenich, Delivery Systems, retrieved from http://www.firmenich.com/portal/page?_pageid=614,143034&_dad=portal&_schema=PORTAL&sid=ds& . . . on Mar. 25, 2004.

Firmenich, Polymer Science, retrieved from http://www.firmenich.com/portal/page?_pageid=1295,189627&_dad=portal&_schema=PORTAL&sid=ps . . . on Mar. 25, 2004.

Image of Life Savers wintergreen mint, on sale prior to Apr. 20, 2004.

Lees et al., Sugar Confectionary and Chocolate Manufacture, Leonard Hill, pp. 165, 183, 184 (1973).

Wrigley's Eclipse breath mints on sale before Apr. 20, 2003.

* cited by examiner

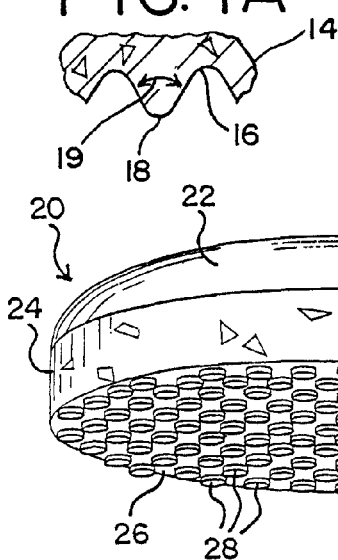
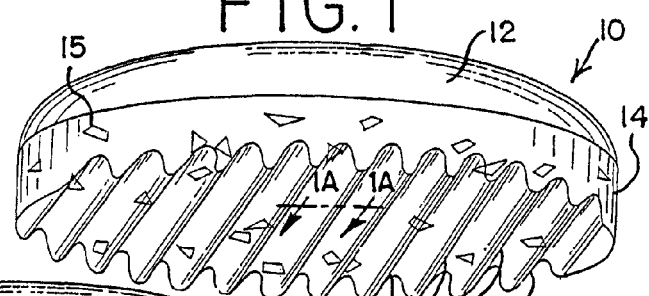
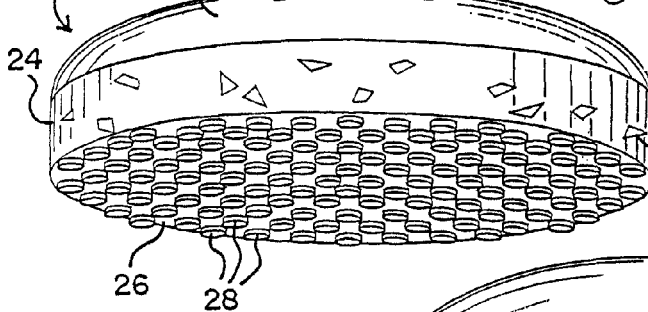
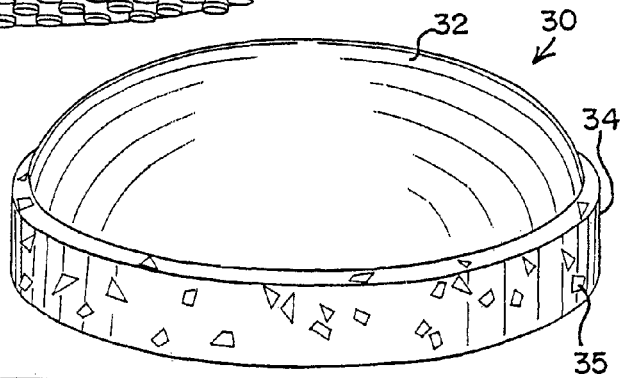
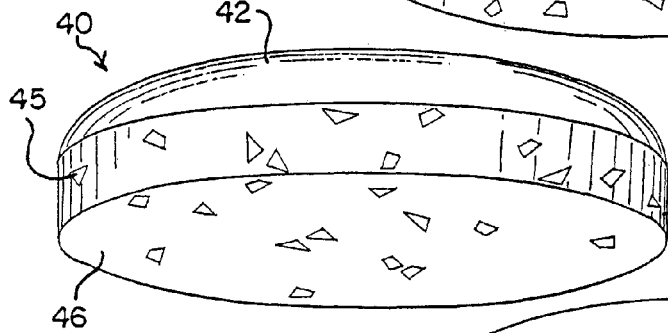
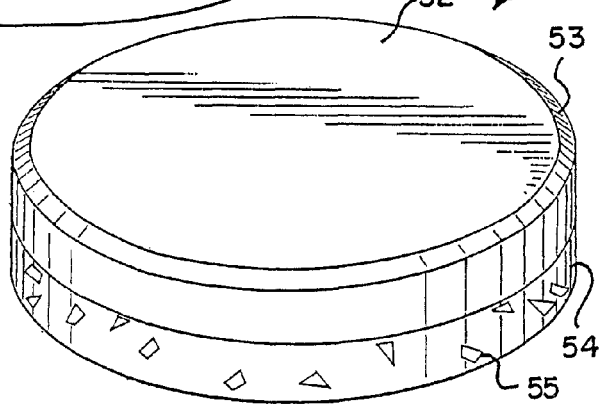

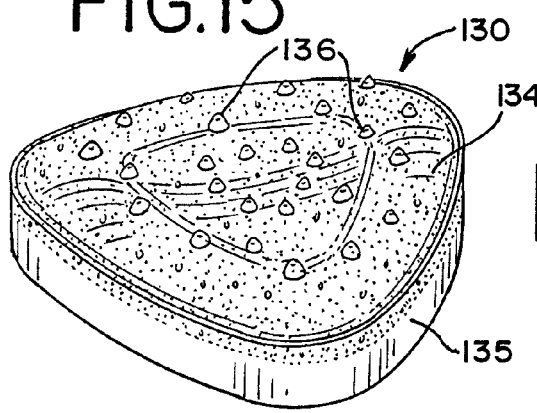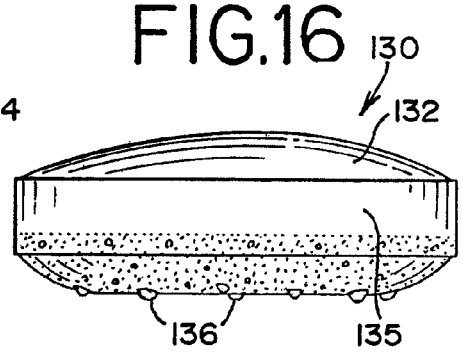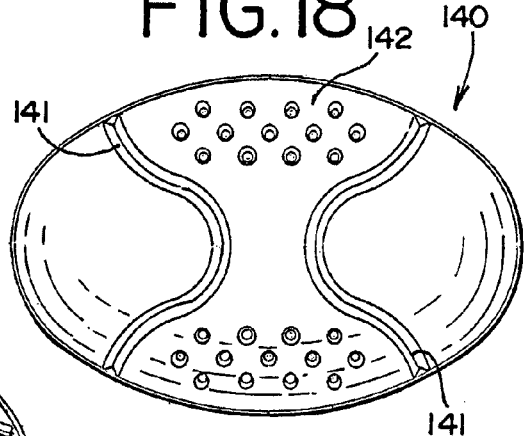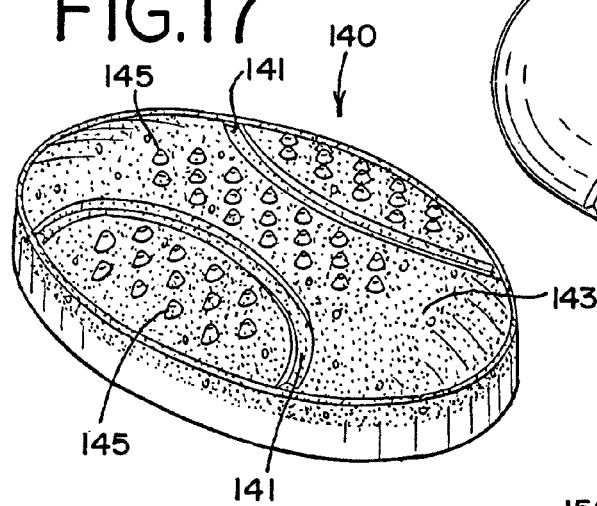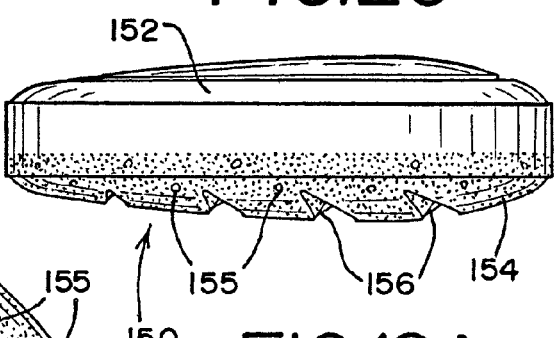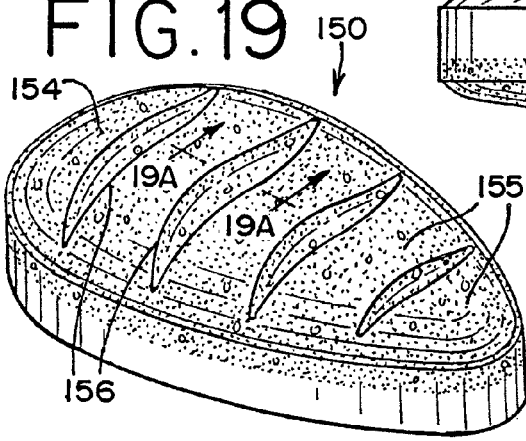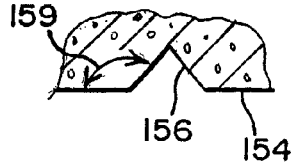

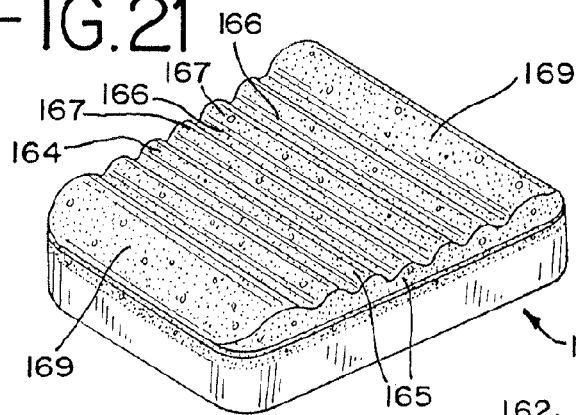
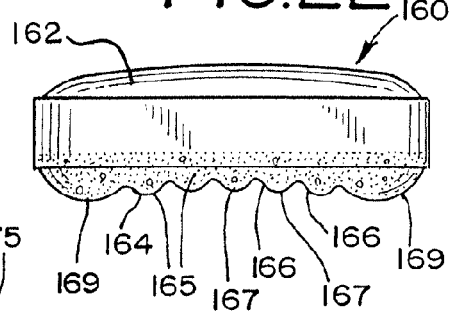
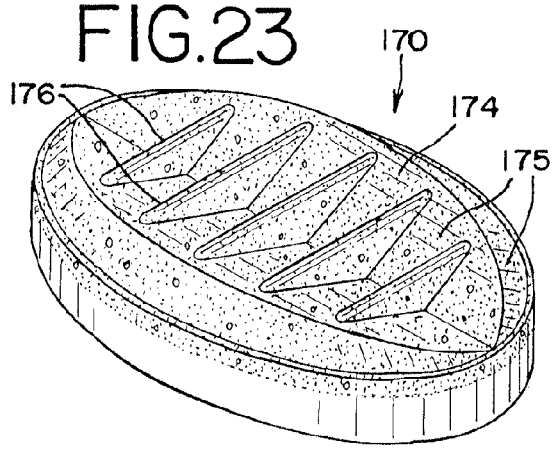
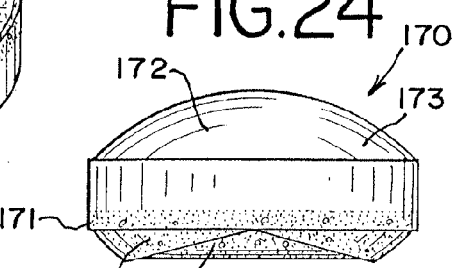
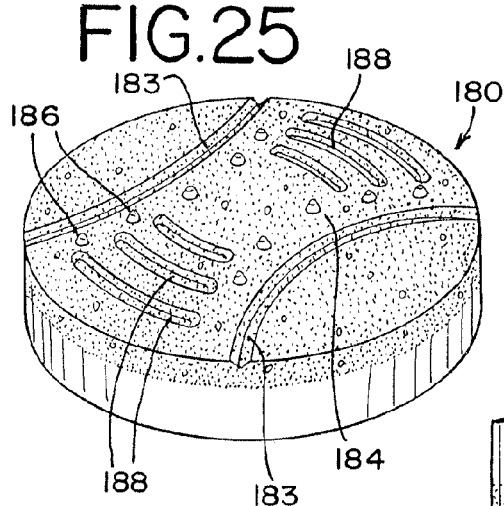
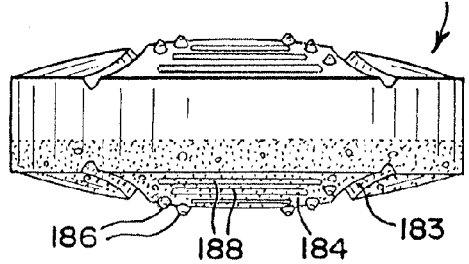

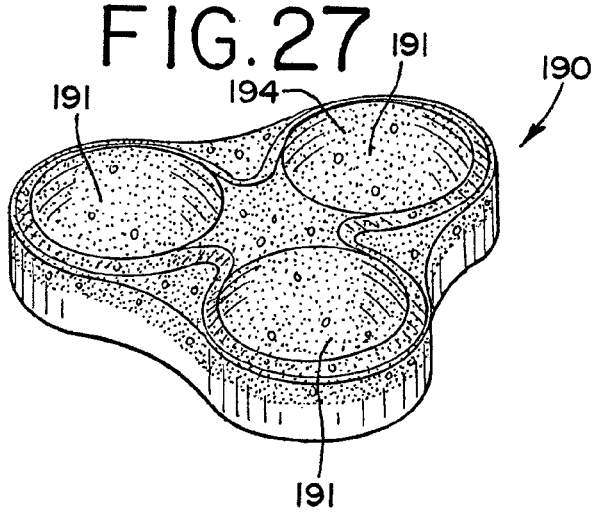
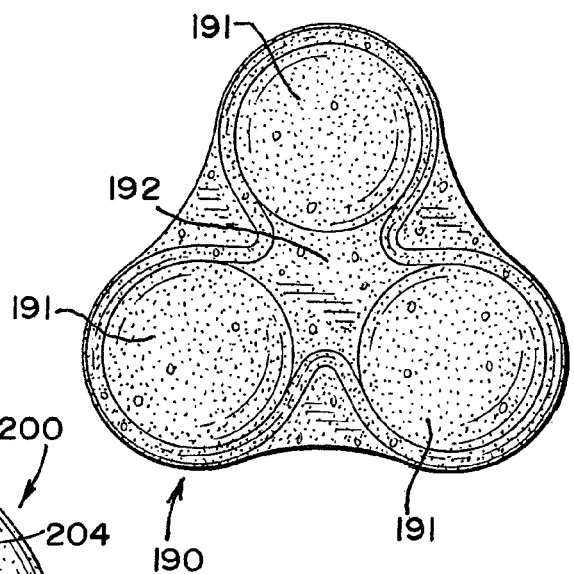
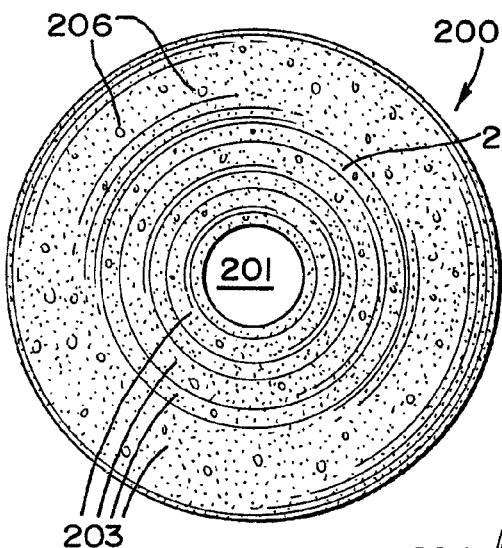
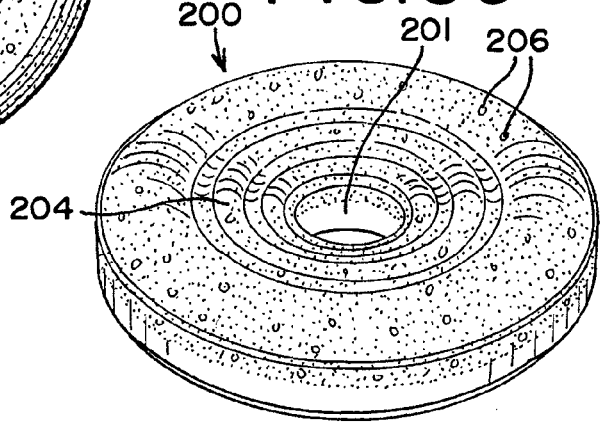

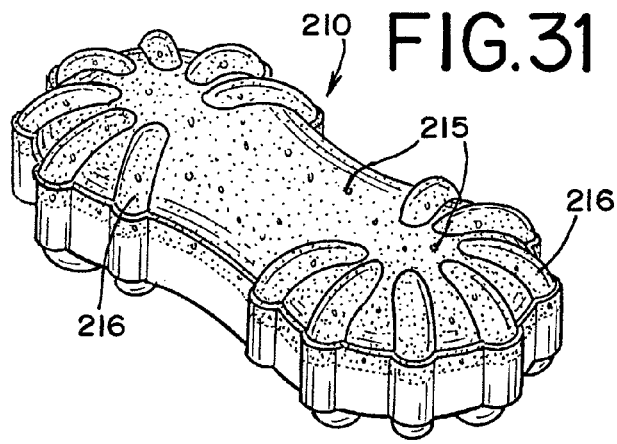
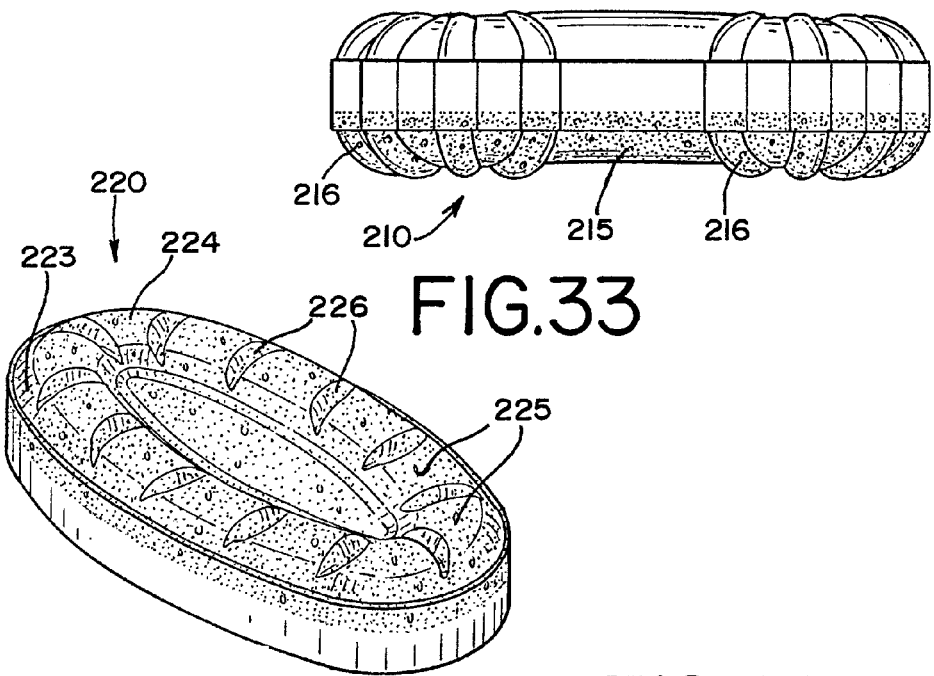
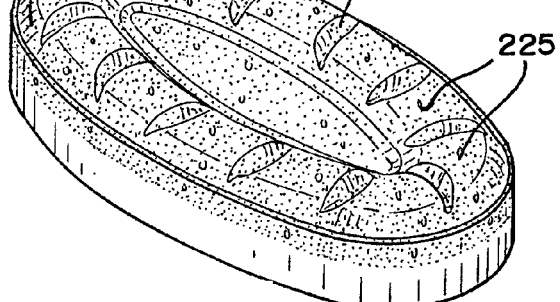
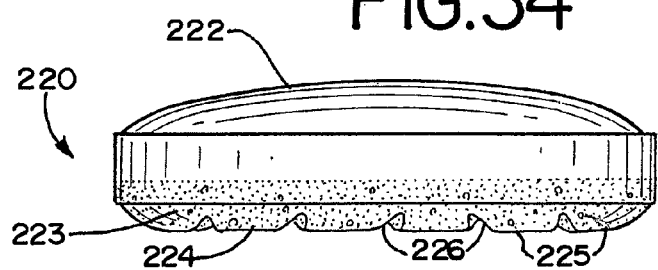

BREATH FRESHENING CONFECTIONERY PRODUCTS AND METHODS OF MAKING AND USING SAME

REFERENCE TO EARLIER FILED APPLICATIONS

The present application is a continuation of U.S. patent application Ser. No. 11/550,940, filed Oct. 19, 2006, which is a continuation of PCT Application Ser. No. PCT/US2005/013544, filed Apr. 20, 2005, designating the United States, which in turns claims the benefit of the filing date under 35 U.S.C. §119(e) of the following Provisional U.S. Patent Applications: 1) Ser. No. 60/564,053, filed Apr. 20, 2004; 2) Ser. No. 60/650,785, filed Feb. 7, 2005 and 3) Ser. No. 60/650,786, filed Feb. 7, 2005; each of which is hereby incorporated by reference in its entirety.

BACKGROUND

The present invention relates to confectionery products having breath freshening attributes, particularly pressed tablets, deposited hard candy and tablet chewing gum, and methods of producing and using such confectionery products. More particularly, the invention relates to confectionery products having an abrasive surface that is suitable for scrubbing the top surface of the human tongue.

The existence of bad breath has long been a serious problem. Mouth odor is embarrassing at the least, and may diminish personal interactions. The reasons for its occurrence have not been fully understood, and there have been many attempts to overcome its effects. Halitosis, or oral malodor, is thought to be created by degraded epithelial cells of the tongue and the surface of the oral mucosa. It is estimated that 90% of mouth odor is caused by bacterial growth in the food debris trapped between the papillae ridges of the upper (dorsal) surface of the tongue. Volatile sulfur compounds (such as hydrogen sulfide, methyl mercaptan, dimethyl sulfide) are produced by the putrefactive activities of bacteria in the saliva, the gingival crevice, the tongue coating and other places in the oral cavity. Research indicates that volatile sulfur compound formation occurs primarily on the tongue dorsum. The human tongue has folds and grooves in its dorsal surface and the volatile sulfur compounds that are encountered reach the posterior surface area of the tongue, as well as other areas in the oral cavity, and find their way particularly into those folds and grooves and become firmly lodged therein. It is very difficult to dislodge these materials. Tongue coating includes desquamated epithelial cells released from the oral mucosa, leukocytes from periodontal pockets, and bacteria. Leukocytes possess large quantities of sulfur-containing amino acids from which volatile sulfur compounds are made.

Various devices and products have been devised for cleansing the mouth and freshening the breath, notably the toothbrush, dental floss, mouthwash, aromatic candies, and toothpick. However, each of these has disadvantages. The toothbrush is probably the most widely used breath-freshening device. It is generally effective, but suffers from some disadvantages. The use of the toothbrush requires rinsing the mouth with water, thus restricting the use of the toothbrush near a sink. The toothbrush is commonly used with dentifrice, which must be periodically replaced. After use, the toothbrush is wet, and the bristles hold water, thus making the toothbrush inconvenient to carry in a pocket or purse. In addition, the toothbrush can hold and accumulate food particles in its bristles, thus requiring it to be thoroughly cleaned after each use. Furthermore, the toothbrush also may not help to reduce certain food odors, particularly if used without dentifrice. Further, it is not socially acceptable to use toothbrushes in public.

Dental floss, while effective in removing food particles lodged between the teeth, has the disadvantage of needing to be disposed of. After one use, the piece of floss is usually discarded. Also, use of dental floss can be painful, especially for first-time users. Furthermore, use of dental floss normally requires both hands and proximity to a sink for expectorating and a garbage can to discard the used piece of floss, thus the use of dental floss is restrictive to certain locations. Also, dental floss may not be effective for removing certain food odors.

Like dental floss, mouthwash also has the disadvantages of being restrictive to certain locations. Unfortunately mouthwashes do not physically scrape or remove debris from between the papillae on the surface of the tongue. Thus, odor-causing bacterial growth commences within minutes after using these devices. Furthermore, gargling is not appropriate in public and the mouthwash must be expelled after use.

Breath-freshening candies have the disadvantage of merely masking the odor, and not actually removing or breaking down odor-causing particles. Furthermore, some breath-freshening candies, because of their sugar content, may promote tooth decay.

Finally toothpicks are sometimes used to freshen the breath, but they also have some of the same problems as those mentioned above. In addition, if the pick is sharp, it may be dangerous.

Most of the consumer mass-marketed breath-freshener products (gums, mints, rinses, pastes, and strips) do not eliminate the source of bad breath, they just mask breath problems.

U.S. Patent Application Publication No. 2002/0132000 discloses a rough-textured boiled hard candy for treating halitosis. Crystalline hydrogenated or non-hydrogenated saccharides, organic acids and organic acid salts capable of conferring a rough texture are incorporated into the candy composition.

U.S. Patent Application Publication No. 2003/0163149 discloses a breath freshener lollipop, comprising an applicator head affixed to a handle. The applicator head is made of an edible substance intermixed with an antibacterial means and molded with a textured surface for separating the folds of the tongue and accessing the grooves for the purpose of eliminating the precursors of volatile sulfur compounds.

Even with these many products there is still room for improvement. For example, the use of a lollipop for scrubbing the tongue has the disadvantage that it cannot be done very discretely, as the handle has to be manipulated and protrudes out of the mouth. Compared to boiled hard candy products, pressed mints have lower costs for ingredients (at least for sugarless products), lower energy and labor costs, lower capital costs and lower setup costs. Pressed products are more closely associated with breath freshening in the minds of consumers in at least some markets. The slightly rough texture of compressed products provides better traction against the roof of the mouth than the smoother surface of a boiled candy. Life Saver® pressed mints are not sold as a breath-freshening product, and the mints cannot be used to scrape the tongue because surface lettering on the mints is not high enough to provide sufficient tongue cleaning before the lettering is eroded. The hardness of the product may not be sufficient for it to effectively clean the tongue, in part because it dissolves too quickly. Thus there is still a need for a product which can be used to discretely scrub the tongue and reduce or remove tongue plaque, yet still be enjoyed as a confectionery. Furthermore, it is known that saliva reduces the amount of residual food debris on the surface of teeth and gums. Thus, such a product would preferably induce saliva secretion over an extended period of time, such as by the release of flavorings which provoke the reflex release of saliva. Therefore, the need exists for a product and method of freshening breath that is safe, portable, discrete and effective.

BRIEF SUMMARY OF THE INVENTION

Confectionery products have been invented that can be discretely used to scrub the tongue, thereby providing breath freshening and other oral health benefits. Preferred embodiments have a smooth surface on one side and an abrasive surface on the other side. The smooth surface can be held against the roof of the mouth while the tongue scrubs across the abrasive surface. The term "abrasive" means that the surface is effective, either immediately when placed in the mouth or after starting to be dissolved, to remove odor causing deposits on the tongue. Of course the abrasive surface may also be suitable to clean other soft oral surfaces, such as the inside of the cheek. The term "smooth" means that the surface, even after being partially dissolved, does not cause irritation against the gums or roof of the mouth. The preferred confectionery products are hard confectionery products, which means that they retain their shape in the mouth and slowly dissolve. These products are primarily consumed by sucking, and will generally shatter if bitten sufficiently hard. The confectionery products may also include chewing gum products, including tablet chewing gum.

In a first aspect, the invention is a confectionery product comprising a first side and a second side generally opposite to the first side; the first side comprising a domed, non-abrasive surface; and the second side comprising an abrasive surface that is suitable for scrubbing the top surface of a tongue within the oral cavity.

In a second aspect, the invention is a confectionery product comprising a first confectionery composition and a second confectionery composition different than the first composition, the second composition comprising an abrasive surface that is suitable for scrubbing the top surface of a tongue.

In a third aspect, the invention is a confectionery product comprising a first side and a second side generally opposite to the first side; the first side comprising a concave surface; and the second side comprising an abrasive surface that is suitable for scrubbing the top surface of a tongue within the oral cavity.

In a fourth aspect, the invention is a confectionery product comprising a confectionery material comprising abrasive inclusions; and the confectionery material being formed into a product having a piece size with no dimension greater than about 25 mm and at least one formed, uneven surface, the abrasive inclusions and formed, uneven surface together forming an abrasive scrubbing surface that is suitable for scrubbing the top surface of a tongue.

In a fifth aspect, the invention is a confectionery product comprising a first side and a second side generally opposite to said first side; the first side comprising a smooth surface; and the second side comprising an abrasive surface that is suitable for scrubbing the top surface of a tongue, the second side being made of a confectionery material comprising abrasive inclusions.

In a sixth aspect, the invention is a confectionery product comprising a piece size with no dimension greater than about 25 mm; and an abrasive surface that is suitable for scrubbing the top surface of a tongue, comprising a formed, uneven surface having a washboard shape, an uneven surface having a grid pattern, or the abrasive surface being made of a confectionery material comprising abrasive inclusions formed of a material selected from the group consisting of solid matrices of carbohydrates, solid matrices of polyols, extruded carbohydrates, extruded polyols and mixtures thereof: or one or more granular bicarbonates and one or more granular food acids that combine in the oral cavity to produce an effervescent action. Alternatively, granular, edible inorganic salts may be used.

In a seventh aspect, the invention is a process for making a confectionery product comprising the steps of: a) producing a first confectionery composition and depositing it in a mold to form a first layer of the confectionery product, the mold creating an abrasive surface on the first layer; and b) producing a second confectionery composition and depositing it on the first layer to form a second layer.

In an eighth aspect, the invention is a method of removing bacteria from the top surface of a human tongue comprising: a) placing a confectionery product having a first side and a second side generally opposite to said first side in an oral cavity, the first side comprising a domed, non-abrasive surface, and the second side comprising an abrasive surface, with the abrasive surface contacting the top surface of the tongue; and b) causing the abrasive surface of the confectionery product to be scraped across the top surface of the tongue while the oral cavity is closed to thereby loosen bacteria on the top surface of the tongue.

In a ninth aspect, the invention is a pressed tablet made from a compressible composition and having at least one abrasive surface suitable for cleaning the surface of a human tongue in an oral cavity, the tablet having a hardness of between about 18 Kp and about 35 Kp.

In a tenth aspect, the invention is a method of making a hard pressed tablet suitable for cleaning the surface of a human tongue comprising a) providing a compressible composition; and b) compressing the compressible composition into a tablet with sufficient pressure to produce a tablet having a hardness of between about 18 Kp and about 35 Kp, the tablet having at least one abrasive surface suitable for cleaning the surface of a human tongue in an oral cavity.

In an eleventh aspect, the invention is a method of making a hard pressed tablet suitable for cleaning the surface of a human tongue comprising a) providing a compressible composition; and b) compressing the compressible composition into a tablet with a force of at least 5000 pounds to produce a tablet having at least one abrasive surface suitable for cleaning the surface of a human tongue in an oral cavity.

In a twelfth aspect, the invention is a method of making a hard pressed tablet suitable for cleaning the surface of a human tongue comprising a) providing a compressible composition; and b) compressing the compressible composition into a tablet with a pressure of at least 22,000 psi to produce a tablet having at least one abrasive surface suitable for cleaning the surface of a human tongue in an oral cavity.

In a thirteenth aspect, the invention is a method of removing bacteria from the top surface of a human tongue comprising a) placing a pressed tablet made from a compressible composition and having at least one abrasive surface suitable for cleaning the surface of a human tongue in an oral cavity, with the abrasive surface contacting the top surface of the tongue, the tablet having a hardness of between about 18 Kp and about 35 Kp; and b) causing the abrasive surface of the pressed tablet to be scraped across the top surface of the tongue while the oral cavity is closed to thereby loosen bacteria on the top surface of the tongue.

Other aspects of the invention may combine two or more of the features from any of the foregoing aspects of the invention.

The preferred embodiments of the invention provide a confectionery product that can be placed in the mouth and discretely used to scrub the tongue and remove particles of food and bacteria. The domed shape of preferred embodiments fits into the roof of the mouth, or the concave shape can be used to form a vacuum, to hold the confectionery product in place while the tongue is scrubbed across its lower surface. The top surface is preferably smooth so as to not cause irritation in the mouth. The hard confectionery products have an advantage that they may be completely consumed. These and other advantages of the preferred embodiments of the invention will be best understood in light of the attached drawings.

BRIEF DESCRIPTION OF THE DRAWINGS

FIG. 1 is a bottom perspective view of a first embodiment of a confectionery product of the present invention.

FIG. 1A is a cross-sectional view taken along line 1A-1A of FIG. 1.

FIG. 2 is a bottom perspective view of a second embodiment of a confectionery product of the present invention.

FIG. 3 is a top perspective view of a third embodiment of a confectionery product of the present invention.

FIG. 4 is a bottom perspective view of a fourth embodiment of a confectionery product of the present invention.

FIG. 5 is a top perspective view of a fifth embodiment of a confectionery product of the present invention.

FIG. 15 is a bottom perspective view of a thirteenth embodiment of a confectionery product of the present invention.

FIG. 16 is a side elevational view of the product of FIG. 15

FIG. 17 is a bottom perspective view of a fourteenth embodiment of a confectionery product of the present invention.

FIG. 18 is a top plan view of the product of FIG. 17.

FIG. 19 is a bottom perspective view of a fifteenth embodiment of a confectionery product of the present invention.

FIG. 19A is a cross-sectional view taken along line 19A-19A of FIG. 19.

FIG. 20 is a side elevational view of the product of FIG. 19.

FIG. 21 is a bottom perspective view of a sixteenth embodiment of a confectionery product of the present invention.

FIG. 22 is a side elevational view of the product of FIG. 21.

FIG. 23 is a bottom perspective view of a seventeenth embodiment of a confectionery product of the present invention.

FIG. 24 is a side elevational view of the product of FIG. 23.

FIG. 25 is a bottom perspective view of an eighteenth embodiment of a confectionery product of the present invention.

FIG. 26 is a side elevational view of the product of FIG. 25.

FIG. 27 is a bottom perspective view of a nineteenth embodiment of a confectionery product of the present invention.

FIG. 28 is a bottom plan view of the product of FIG. 27.

FIG. 29 is a bottom plan view of a twentieth embodiment of a confectionery product of the present invention.

FIG. 30 is a bottom perspective view of the product of FIG. 29.

FIG. 31 is a bottom perspective view of a twenty-first embodiment of a confectionery product of the present invention.

FIG. 32 is a side elevational view of the product of FIG. 31.

FIG. 33 is a bottom perspective view of a twenty-second embodiment of a confectionery product of the present invention.

FIG. 34 is a side elevational view of the product of FIG. 33.

DETAILED DESCRIPTION OF THE DRAWINGS AND THE PRESENTLY PREFERRED EMBODIMENTS

Figure 6:
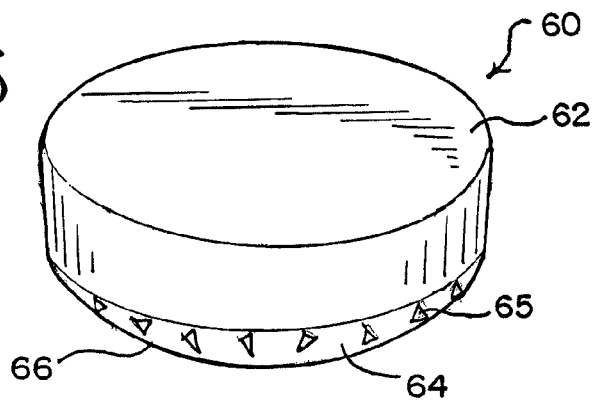
FIG. 6 is a top perspective view of a sixth embodiment of a confectionery product of the present invention.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

There are several presently preferred embodiments of the invention. Each of the embodiments is common in that they comprise confectionery products that include an abrasive surface. Some of the products are made with layers, and made of separate confectionery compositions. The abrasive surface may be provided by abrasive particles, also referred to as inclusions, in the confectionery, or may be provided by a formed, uneven surface, or may have both abrasive inclusions and a formed, uneven surface. The formed surface may be molded using a compression die. When the abrasive surface is a formed, uneven surface, the piece will preferably have projections or grooves which expose a defined convex angle of not more than 135 degrees. Alternatively, if the piece comprises inclusions to provide the abrasive surface, the inclusions will preferably be hard particles of at least 100 microns, preferably at least 200 microns, and most preferably at least 400 microns in size, and which are less soluble than the surrounding matrix. The inclusions may be present on the surface to begin with, or may be exposed as the product is dissolved in the mouth to produce a perceivably rough surface.

In each instance the abrasive surface is suitable for scrubbing the top surface of the tongue within the oral cavity. The confectionery may be made of a pressed tablet, a deposited hard candy, a tablet chewing gum, or any other type of confectionery that is suitable to provide such an abrasive surface. Pressed tablets with sufficient hardness are presently preferred embodiments of the invention.

The abrasive surface is preferably provided at least in part by surface features having at least one scraping edge. The at least one scraping edge may be located on a protrusion on the abrasive surface. For example, the scraping edge may be formed by an acute angle on the protrusion. The scraping edge may also be formed on the edge of a groove in the abrasive surface. Preferably the abrasive surface is provided at least in part by surface features comprising either or both projections and grooves, the projections having a height of at least 0.015 inches and the grooves having a depth of at least 0.008 inches. More preferably the surface features will comprise projections having a height of at least 0.018 inches and/or grooves having a depth of at least 0.009 inches. Most preferably the height of the projections will be at least 0.020 inches and/or the depth of the grooves at least 0.010 inches.

Alternatively the at least one abrasive surface may be provided by abrasive particles in the confectionery composition. The abrasive particles may either be incorporated into the composition or located on the abrasive surface of the tablet. Of course the abrasive particles may be embedded in a surface layer making up the abrasive surface of the product.

A first preferred embodiment is shown in FIG. 1. A confectionery product in the form of a pressed tablet 10 has a generally cylindrical shape with two layers, a top layer 12 and a bottom layer 14. The tablet 10 has a first side, formed by a generally domed shape top of the first layer, and a second side 16 generally opposite to the first side. The height of the tablet 10 is less than the diameter of the cylindrical shape. The second side 16, forming one of the ends of the cylinder, comprises an abrasive surface that is suitable for scrubbing the top surface of the tongue within the oral cavity. In the embodiment of tablet 10, the second side 16 is generally planer with a plurality of raised portions thereon. In this embodiment, the abrasive surface comprises a formed, uneven surface having a washboard shape with ridges 18. The ridges 18 extend away from surface 16 in a triangular fashion, as shown in FIG. 1A. The ridges 18 define projections which expose a convex angle 19. The angle 19 of the sides of the triangle is less than 135 degrees. In addition, the abrasive surface is provided by abrasive inclusions 15 in the composition of the confectionery making up the second layer 14.

The first layer 12 providing the domed surface is made from a first composition that is different than a second composition making layer 14 providing the abrasive surface 16. Both compositions are preferably confectionery materials. They may differ in many respects, or they may differ only in the fact that the second composition has abrasive inclusions 15 mixed into it. Preferably the first and second compositions will be different in color from one another. For example, the first composition making top layer 12 may be generally white, while the second composition making the second layer 14 may be generally blue.

The first side comprises a non-abrasive, smooth surface. In this embodiment, the dome shape of the top layer 12 is generally shaped to fit the contour of the top of an oral cavity. The interface between the first and second layers is generally parallel to the abrasive surface 16.

Figure 41:
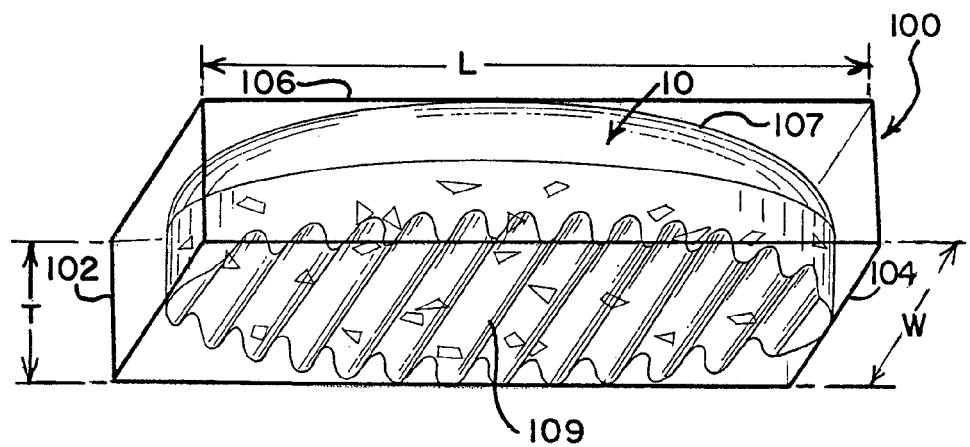
FIG. 41 is a bottom perspective view of the product of FIG. 1 showing an imaginary box that may be used to determine the dimensions of a product.

FIG. 41 shows an imaginary box 100 drawn around the tablet 10. The product thickness is preferably determined by forming an imaginary three dimensional box having three sets of two parallel sides, each side being at right angles to the other sides to which it is connected. Two of the sides are oriented horizontally, and are considered to be top and bottom sides. The product is oriented in the box such that the center of gravity (assuming the product has a uniform density) of the product is as close as possible to the bottom side. The sides each contact the surface of the product, possibly at multiple points, but do not intersect the product. If the product shape is such that numerous boxes could be drawn satisfying the forgoing, the imaginary box used for determining the product's dimensions is the box that has the smallest volume of any possible box meeting the forgoing criteria. The smallest dimension of the box is considered to be the thickness of the product. The next smallest dimension is considered to be the width of the product, and the largest dimension is considered to be the length of the product. For box 100, the height T of side 102 is the thickness of the tablet 10. The length W of side 104 is the width of the abrasive surface, and the length L of side 106 is the length of the abrasive surface. Where the abrasive surface is not generally planer, the abrasive surface is considered as having a width and length equal to the width and length of the product.

Using the forgoing figure, it can be seen that the tablet 10 has a first side 107 and a second side 109 generally opposite to the first side 107. The product thickness is T. The second side 109 comprises an abrasive surface that is suitable for cleaning the top surface of a tongue within an oral cavity. The second side 109 has a width W and a length L, the smallest of which is at least 1.6 times the product thickness T. It is noted that while generally the abrasive surface will be on the bottom of the aforementioned box, the definition of thickness is not dependent thereon. Using the imaginary box definition of thickness, the thickness of the product is simply the smallest dimension of the imaginary box described above.

FIG. 2 shows another embodiment of the invention, pressed tablet 20, with a first layer 22 made of a first composition providing a non-abrasive surface and a second layer 24 made of a second composition. The second composition provides an abrasive surface 26 generally opposite to the domed upper surface on top layer 22. In this embodiment, in addition to the abrasive inclusions 25, the abrasive surface 26 is unevenly formed with a multitude of small, round protrusions 28.

FIG. 3 shows a pressed tablet 30 again made with two distinct layers, top layer 32 and bottom layer 34. The tablet 30 is different than the tablets 10 and 20 in that the two layers are not the same diameter. In this case, the diameter of the second layer 34 is larger than the diameter of the first layer 32. Abrasive inclusions 35 provide an abrasive surface on the second layer.

The tablet 40 shown in FIG. 4 again has two layers 42 and 44 made of different compositions. While the top layer 42 provides a domed top surface, the abrasive surface 46 in this embodiment is provided solely by the abrasive inclusions 45.

FIG. 5 shows a tablet 50 with a bottom layer 54 that comprises abrasive inclusions 55 providing an abrasive surface on the bottom of the tablet 50. In this embodiment, the top layer 52 has a smooth surface, but instead of being domed the surface is generally flat, with a beveled corner 53 on the end opposite the abrasive surface.

Figure 7:
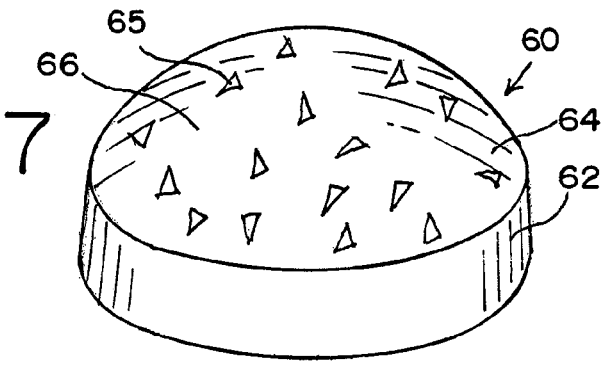
FIG. 7 is a bottom perspective view of the confectionery product of FIG. 6.

The embodiment of FIG. 6 shows a two-part pressed tablet 60. In this embodiment, the first part 62 is made by compressing a first compressible material. Thereafter a second part 64 is made from a second compressible material different than the first compressible material. As seen from the bottom view of FIG. 7, the second part 64 has an exposed surface 66 on the bottom of candy piece 60. Abrasive inclusions 65 in the second composition provide the second part 64 with an abrasive surface that is suitable for scrubbing the top surface of the tongue. The composition of first part 62 may also be colored differently than the second part.

Figure 8:
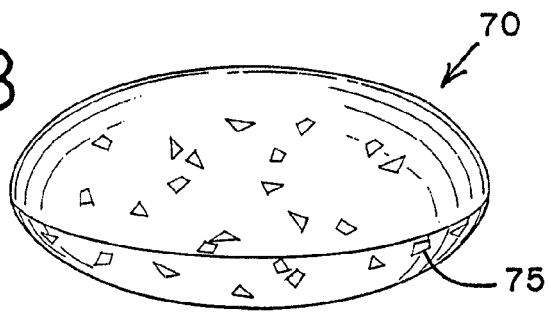
FIG. 8 is a top perspective view of a seventh embodiment of a confectionery product of the present invention.

Pressed tablet 70 shown in FIG. 8 does not have distinct layers, and may be formed all of one composition. The composition comprises abrasive inclusions 75 to provide an abrasive surface opposite the generally domed top surface on the tablet. The abrasive inclusions in this embodiment comprise solid matrices of carbohydrates, solid matrices of polyols, extruded carbohydrates or extruded polyols, and also carry a flavor.

Figure 9:
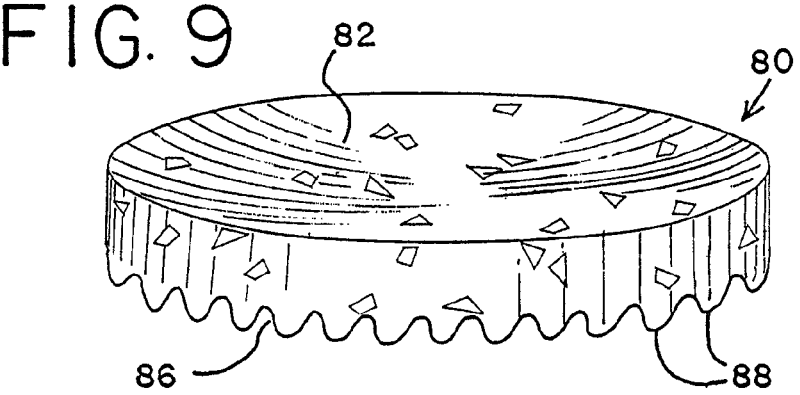
FIG. 9 is a top perspective view of an eighth embodiment of a confectionery product of the present invention.

Pressed tablet 80 shown in FIG. 9 is also made with only a single composition. Rather than having a domed top surface, the top surface 82 of tablet 80 is concave in shape. The opposite, bottom surface 86 is generally planer and has a formed, uneven surface 86 made up of ridges 88 in a washboard pattern. It is believed that a person can suck on the tablet 80 in such a way that a partial vacuum can be formed between the concave surface 82 and the roof of their mouth. This vacuum will then help to hold the tablet 80 in place while the tongue is scrubbed across the abrasive surface 86. The tablet 80 may be oblong rather than round to help fit against the palate.

Figure 10:
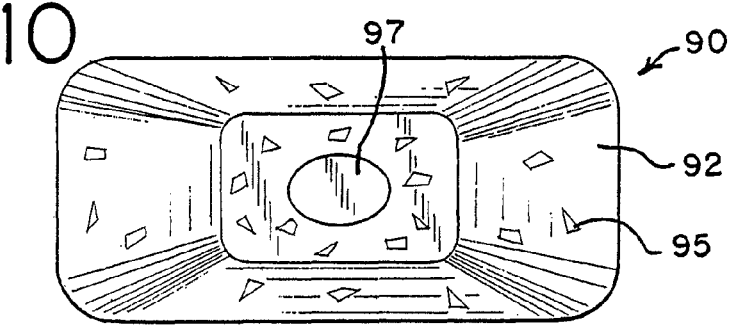
FIG. 10 is a top view of a ninth embodiment of a confectionery product of the present invention.
Figure 11:
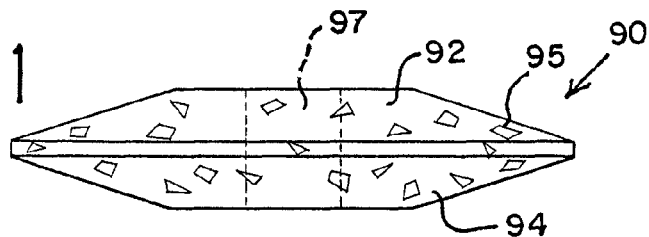
FIG. 11 is a side elevational view of the confectionery product of FIG. 10.

The embodiment shown in FIGS. 10 and 11 comprises a pressed mint 90 having a center 97 that is a different confectionery composition than the confectionery composition making up the top layer 92 and bottom layer 94. Further, if desired, these two layers may be the same material, and not distinct layers. The composition of the outer shell includes abrasive inclusions 95 and thus provides an abrasive surface, whereas the material making the center 97 may be colored blue or some other color, and include mint flavoring and other breath freshening ingredients.

Figure 12:
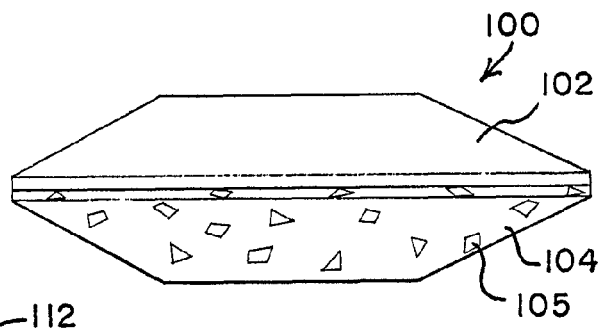
FIG. 12 is a side elevational view of a tenth embodiment of a confectionery product of the present invention.

The tablet 100 shown in FIG. 12 has the same general shape as pressed mint 90, but is made of two layers as in the earlier embodiments. The first layer 102 may include breath freshening ingredients, while the second layer 104 includes abrasive inclusions 105 that provide an abrasive surface.

Figure 13:
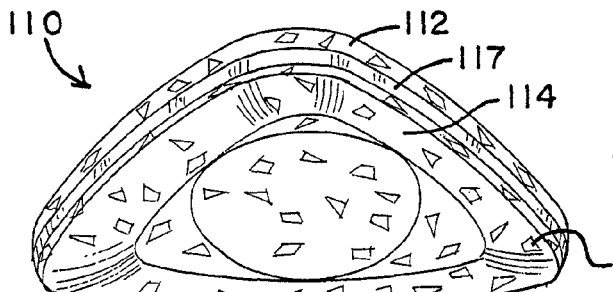
FIG. 13 is a bottom perspective view of an eleventh embodiment of a confectionery product of the present invention.

The tablet 110 in FIG. 13 has a generally triangular shape and three layers. The bottom layer 114, and optionally the top layer 112 as shown in FIG. 13, includes abrasive inclusions 115, while the middle layer 117 contains a breath freshening ingredient and is a different color than layers 112 and 114. Thus, while the top and bottom layer confectionery compositions are both different than the composition of the middle layer confectionery, at least the bottom layer is of a confectionery composition that comprises an abrasive surface suitable for scrubbing the top surface of the tongue.

Figure 14:
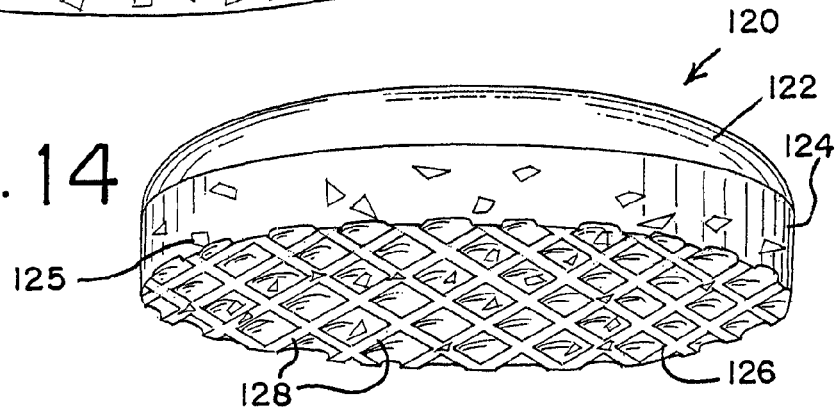
FIG. 14 is a bottom perspective view of a twelfth embodiment of a confectionery product of the present invention.

FIG. 14 shows an embodiment of a pressed tablet 120. The tablet has a top layer 122 made of a first confectionery material and a bottom layer 124 made of a second confectionery material. The second confectionery material comprises abrasive inclusions 125, and is formed with an uneven surface 126. In this embodiment, the ridges 128 form a grid pattern. The abrasive surface is generally planer except for the features making it abrasive.

Another embodiment of a pressed tablet 130 is shown in FIGS. 15 and 16. The tablet 130 has an abrasive bottom surface 134 comprising a plurality of individual bumps 136 protruding from the abrasive surface. The bumps 136 have a plurality of different sizes. The bumps 136 are shown as generally circular, but they could be of other shapes. The top surface 132 does not include bumps. The bottom half of the product includes abrasive inclusions 135. The top surface 132 is generally concave while the bottom surface 134 is generally convex. The bumps 136 and inclusions 135 provide the bottom surface of the pressed tablet 130 with an abrasive surface suitable for cleaning the surface of a human tongue in an oral cavity.

Tablet 140, shown in FIGS. 17 and 18, is elliptical in its major cross-section. The outer surface of the shape includes a groove 141 that resembles the joint on the cover of a baseball. The abrasive surface on the bottom of tablet 140 is provided by bumps 145 extending from the lower hemispherical portion of the shape, as well as abrasive inclusions 143 in the material used to form the bottom half of the tablet, and to a small extent the grooves 141. The top surface 142 may include bumps and the grooves 141 as shown, or may be smooth.

Pressed tablet 150 shown in FIGS. 19 and 20 also has a bottom surface 154 with grooves 156. The grooves 156 are wavy, and extend generally parallel to each other across the bottom width of the tablet. As best seen in FIG. 19A, the grooves 156 intersect with the bottom surface 154 to expose a defined convex angle 159 of not more than 135 degrees. The tablet 150 is generally teardrop shaped. The bottom surface 154 also includes abrasive inclusions 155. However, the top surface 152 of the tablet 150 is generally smooth.

FIGS. 21 and 22 show a generally keystone shaped pressed tablet 160. While the top surface 162 is generally smooth, the bottom surface 164 has a plurality of grooves 166 running across the width of the keystone. In this product, the grooves 166 separate humps 167. The humps 167 and abrasive inclusions 165 provide an abrasive surface to the product. The product may be made of two different materials, with the top surface 162 being made of one material that does not contain abrasive inclusions, and the humps 167 being made of another material that does contain the abrasive inclusions 165. The humps 169 on the ends may be larger than the humps 167 in the middle portion of tablet 160.

In the pressed tablet 170 shown in FIGS. 23 and 24, the abrasive surface is provided by a plurality of generally parallel ridges 176 extending generally perpendicular from the bottom side 174 of the tablet 170. The abrasive bottom surface 174 is generally concave except for the features making it abrasive. The top surface 172 is generally smooth. The ridges 176 each have a generally straight outer surface, but in an alternate embodiment (not shown) the ridges could extend further and have a generally arcuate outer surface. The plurality of ridges comprises at least three ridges, more preferably five ridges. In the embodiment show, all of the ridges have the same height, but in an alternate embodiment, the ridges toward the middle of the group of ridges could extend outwardly of the ridges on the sides of the group. The tablet 170 may be made with two layers; the bottom layer 171 forming the ridges 176 and bottom surface 174 may contain abrasive inclusions 175, while the top layer 173 is made without the inclusions.

As shown in FIGS. 25 and 26, another pressed tablet 180 is generally circular in shape in plan view. The abrasive bottom surface 184 comprises a plurality of generally circular bumps 186 and a plurality of curved protrusions 188. Two grooves 183 are also formed in the bottom surface 184. The bumps 186, protrusions 188 and grooves 183 all contribute to providing the bottom of the tablet with an abrasive surface. The top surface 180 may have bumps and protrusions, as shown, or the top of tablet may be smooth.

The tablet 190 shown in FIGS. 27 and 28 is generally triangular in plan view. The shape includes three orbs 191, one at each apex of the triangle. The bottom abrasive surface 194 is provided by inclusions used to make the lower half of the tablet. The inclusions in the bottom surface 192 between the orbs, and particularly in the orbs, provide a surface suitable for scrubbing the tongue.

As shown in FIGS. 29 and 30, the tablet 200 is also generally circular in shape in plan view. The tablet 200 has an open center 201. The tablet comprises a shape depicting a plurality of concentric rings 203. The rings 203 themselves and inclusions 206 contained in the material making up the bottom half of the tablet provide the bottom surface 204 of the tablet 200 with an abrasive surface. The upper surface may be smooth or may express the concentric ring shape.

The shape of the tablet 210 shown in FIGS. 31 and 32 is generally a figure eight in plan view. The shape includes ridges 216 extending outwardly from the perimeter of the ends of the figure eight. The ridges extend from the top, around the sides, and onto the bottom or each lobe of the figure eight. The ridges 216 and abrasive inclusions 215 in the material making up the bottom half of the tablet provide the abrasive surface.

FIGS. 33 and 34 show another pressed tablet 220 of the present invention, having a generally oval shape. While the top surface 222 is generally convex, the bottom surface 224 is generally concave. In this embodiment, the tablet has a smooth top surface 222 generally opposite to the abrasive bottom surface 224. The abrasive surface 224 includes a plurality of grooves 226 formed in a toroidal member 223 forming the bulk of the bottom surface. The grooves 226 extend radially across the toroidal member 223. The grooves preferably have a depth of at least 0.008 inches. The edges of the grooves each form a scraping edge. The composition of which the bottom surface is made also includes abrasive inclusions 225, which cooperate along with the grooves 226 to provide the abrasive surface.

Figure 35:
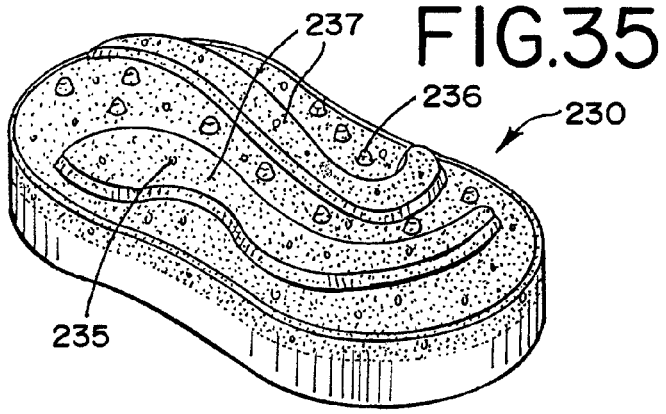
FIG. 35 is a bottom perspective view of a twenty-third embodiment of a confectionery product of the present invention.
Figure 36:
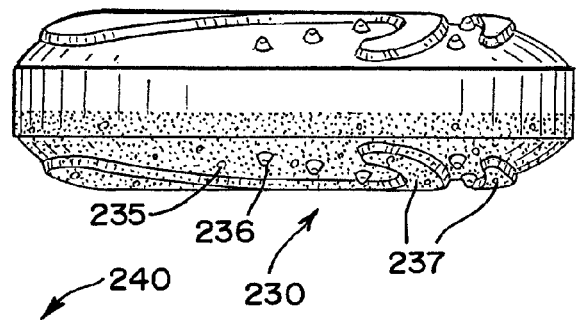
FIG. 36 is a side elevational view of the product of FIG. 35.

Tablet 230 shown in FIGS. 35 and 36 also has somewhat of a figure eight shape. The product may be made of two different materials. At least the bottom half of the tablet is made of a material containing inclusions 235. The bottom surface also includes ridges 237 have scraping edges and bumps 236 formed to provide an abrasive surface. The top surface may have ridges and bumps as shown, or be smooth.

Figure 37:
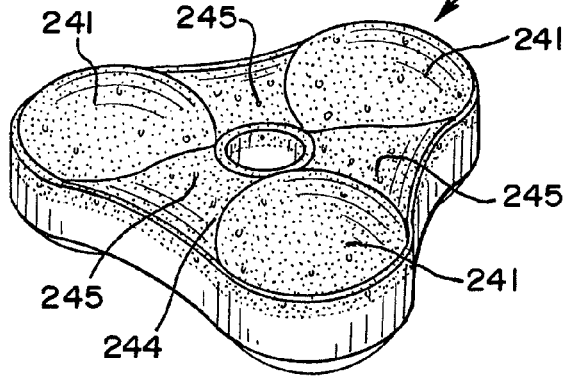
FIG. 37 is a bottom perspective view of a twenty-fourth embodiment of a confectionery product of the present invention.
Figure 38:
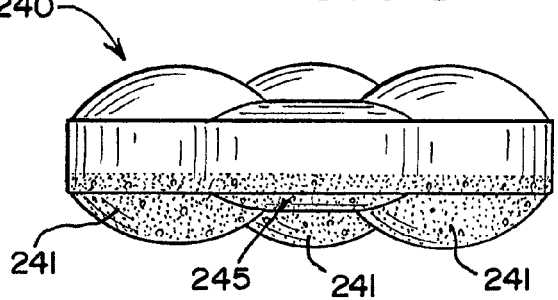
FIG. 38 is a side elevational view of the product of FIG. 37.

The tablet 240 shown in FIGS. 37 and 38 is also generally triangular in plan view. The shape includes three orbs 241, one at each apex of the triangle. The center of the triangle is open. The connections 245 between the orbs 241 are not as thick as the orbs 241. The bottom abrasive surface 244 is provided be abrasive inclusions 245 in the material.

Figure 39:
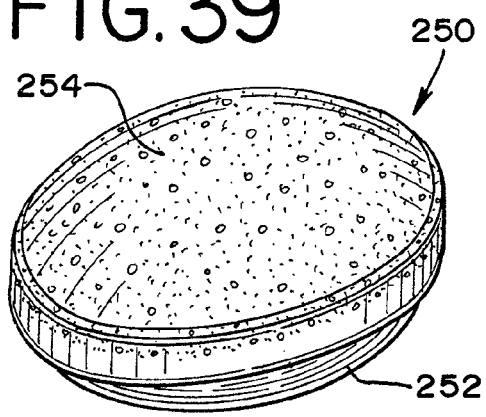
FIG. 39 is a bottom perspective view of a twenty-fifth embodiment of a confectionery product of the present invention.
Figure 40:
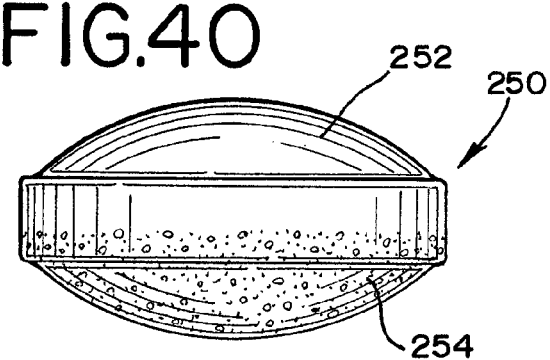
FIG. 40 is a side elevational view of the product of FIG. 39.

The oval tablet 250 shown in FIGS. 39 and 40 has a lower half 254 made with inclusions, thus providing an abrasive surface suitable to clean the tongue. The top half 252 is smooth and may be held against the roof of the mouth while the tongue is scraped across the bottom surface.

While many of the products shown in the drawings are described as being pressed tablets, they could also be made from boiled hard candies. A preferred product will have a piece weight of between about 1 and about 2 grams. For pressed tablets, the preferred piece weight will be about 1 gram. For deposited hard candy pieces, the preferred weight will be between about 1.5 and about 2 grams. The product thickness will preferably be between about 1/16 and about 1/2 inches, and will preferably be at least about 1/8 inch. The smallest of the length and width of the product is preferably between about 1/4 and about 1 inch. The greatest of the length and width of the product is preferably less than 1 1/2 inches. Preferably the pieces will be sized so that they have no dimension greater than about 25 mm. For a cylindrical shaped piece with a diameter greater than its height, this means that the diameter will be less than about 25 mm. Most preferably the pieces will be between about 15 and about 20 mm in their longest dimension.

While the figures show several preferred shapes, it is contemplated that other shapes can be used. Further, surface markings may be included on the products, such as a letter or other indicia.

A preferred confectionery composition will be sugarfree, and may contain one or more antibacterial agents. In addition to, or other than mint flavors, other flavoring agents can be included in the confectionery products. Physiological cooling agents may be included in the products, as well as other ingredients that give a tingling sensation. In the case of products with multiple layers, each layer may have different flavoring agents or levels. In one embodiment, the confectionery product may comprise a coating layer covering at least a portion of the product. In that case, the coating layer may contain flavoring agents at a level higher than any flavoring agents in the remainder of the product.

The particle size of the preferred abrasive inclusions should predominantly be at least 100 microns, with a maximum of 2000 microns (0.1-2 mm). Some preferred abrasive inclusions have a particle size range of about 200 to 600 microns, others are 600 to 1200 microns, and still others may be larger, up to 2000 microns. A preferred range is 200 to 1000 microns. If the abrasive inclusions include a wide range of particle sizes, then the foregoing ranges describe the particle sizes of the majority (from a weight standpoint) of the particles.

The abrasive inclusions may be made from a number of different materials, including crystalline sugars or polyols; solid matrices of carbohydrates, polyols or mixtures; or extruded carbohydrates, polyols, or mixtures; granular food acids; granular inorganic edible salts, such as calcium phosphate salts and other calcium salts including calcium lactate, calcium carbonate and calcium gluconate, silica, silicate salts and bicarbonates; and mixtures thereof. On the one hand, solid matrices (such as from fluid bed coating or spray drying) and extruded carbohydrates or polyols are preferred because these inclusions may also contain flavors and/or colors. When the inclusions include colors, the abrasive particles will preferably have a contrasting color from the remainder of the compressible composition into which they are added. On the other hand, some inorganic salts are preferred because they have dental benefits, such as tooth remineralization or whitening. Further, abrasive food acids and bicarbonates may be combined to not only provide an abrasive surface, but to give an effervescent effect when placed in the mouth.

U.S. Pat. No. 5,786,017 discloses particulate flavor compositions. U.S. Pat. No. 6,607,771 discloses granules for the controlled release of volatile compounds. European Patent Application Publication No. EP 1 214 892 discloses a number of moisture and oxygen stable compositions. PCT Patent Publication No. WO 01/35764 discloses a spray-dried composition in a carbohydrate substrate. Materials disclosed in these references that provide an abrasive surface suitable for scrubbing the tongue may be used as abrasive inclusions in the present invention. Each of these documents is hereby incorporated by reference.

The pressed tablet may preferably include one or more of the following: anti-microbial agents; physiological cooling agents; breath freshening agents; breath freshening and mouth odor masking flavors; and dental active agents. Preferred anti-microbial agents include cardamom oil, magnolia bark extract, cranberry, geraniol, cinnamaldehyde, peppermint, triclosan, chlorhexidine, cetyl pyridinium chloride (CPC) and mixtures thereof. Preferred physiological cooling agents include menthol, N-2,3-trimethyl-2-isopropyl butanamide, 3-l-menthoxypropane-1,2-diol, N-ethyl-p-menthane-3-carboxamide, menthane ketals, menthyl succinate, isopulegol, menthyl glutarate and mixtures thereof. Preferred breath freshening agents include salts of zinc, salts of copper, polyphenols, mushroom extracts and mixtures thereof. Preferred breath freshening and mouth odor masking flavors include cinnamon, mint, wintergreen, fruit flavors and mixtures thereof. Preferred dental active agents include tooth whiteners, fluoride, stain removers, calcium salts, phosphate salts and mixtures thereof.

There are different methods of making the different products of the present invention. The tablet chewing gum product can be made from directly compressible chewing gum powder. Such free-flowing powder is a material in which the basic ingredients (such as gum base and a bulk sweetener) have already been mixed. Dry flavors, lake colors, fruit acids, if desired, and some lubricant such as magnesium or calcium stearate, are blended together in a powder blender such as a ribbon blender, V-blender or cone blender. If abrasive inclusions are also added, they are blended in as well. Thereafter a tablet press or a briquetting machine can be used to form the products.

The pressed tablets of the present invention can be made using conventional tablet pressing procedures and equipment. The compressible composition comprises one or more materials selected from the group consisting of sugars and sugar alcohols. The compressible composition may comprise a directly compressible sugar, such as sucrose plus a binder. The binder may comprise corn syrup and/or maltodextrin. The compressible composition may also comprise a directly compressible sugar alcohol. In some embodiments, the sugar alcohol may be sprayed with water before compression.

To achieve the desired hardness, the preferred tablets of the present invention will be made in a press using a force of at least 5000 pounds, more preferably at least 6000 pounds, and most preferably at least 7000 pounds. The press will be able to generate a pressure of at least 22,000 psi, preferably at least 26,000 psi, more preferably at least 30,000 psi, and most preferably at least 32,000 psi in the tableting composition.

Tablets of the present invention will have a hardness of between about 18 Kiloponds (Kp) and about 35 Kp, preferably between about 20 Kp and about 35 Kp, and most preferably between about 25 Kp and about 35 Kp. (Kiloponds=kilograms force. This is the standard unit used for tablet hardness testing.) The hardness of the tablet may be measured by a tablet hardness tester, such as a Dr. Schleuniger Pharmatron Tablet Tester 8M. The tablet is placed scrubbing side up with the narrowest dimension between the jaws. The instrument is calibrated and the measurement is taken automatically.

A process for making two-layer boiled hard confectionery products may comprise the steps of producing a first confectionery composition and depositing it in a mold to form a first layer of the confectionery product, the mold creating the abrasive surface on the first layer; and then producing a second confectionery composition and depositing it on the first layer to form a second layer. The second confectionery composition will preferably be deposited at a viscosity and under conditions sufficient to result in the second layer having a domed surface opposite the abrasive surface. The domed surface will preferably be generally shaped to fit the top contour of the oral cavity. This method can thus be used to make products shaped like the tablets shown in FIGS. 1, 2, 4 and 14.

Sometimes a product will be made that uses abrasive particles, but those particles are not present throughout the composition. In that instance, rather than making two separate compositions, one with abrasive inclusions and one without, the abrasive inclusions may be embedded in just one surface as a product is formed. Thus two separate compositions are in the final product, one being the composition as initially produced, and the other being a layer having the same composition but with abrasive inclusions included. In a deposited boiled hard candy, this may be accomplished by placing abrasive inclusions in the bottom of the mold before the boiled hard candy is deposited. In a pressed tablet, the inclusions can be placed in the bottom of the die before the compressible material is added.

The preferred products can be used to removing bacteria from the top surface of a human tongue. This will generally involve placing the confectionery product having a first side and a second side generally opposite to the first side, and a product thickness, inside the oral cavity. The second side comprises the abrasive surface and has a width and a length, the smallest of which is preferably at least 1.6 times the product thickness, with the abrasive surface contacting the top surface of the tongue. The abrasive surface of the confectionery product is scraped across the top of the tongue, preferably while the oral cavity is closed, to thereby loosen bacteria on the top surface of the tongue. Preferably the abrasive surface comprises surface features having at least one scraping edge. Preferably the roof of the oral cavity holds the confectionery product stationary in the oral cavity while the tongue is scraped across the abrasive surface.

The following examples help to explain the invention.

Example 1

Pressed Tablet

| First layer | |
|---|---|
| Sorbitol | 97.99% |
| Peppermint flavor | 0.75% |
| Magnesium stearate | 0.64% |
| Encapsulated flavor | 0.28% |
| Menthol | 0.18% |
| Silicon dioxide | 0.16% |
| Total | 100.0 |

| Second layer | |
|---|---|
| Sorbitol | 95.94% |
| Abrasive inclusions | 2.01% |
| Peppermint flavor | 0.75% |
| Magnesium stearate | 0.64% |
| Encapsulated flavor | 0.28% |
| Menthol | 0.18% |
| Blue color | 0.04% |
| Silicon Dioxide | 0.16% |
| Total | 100.0 |

The materials are mixed together as powders. The second layer can be added first to the die formed tablet press and given a precompression. The top or first layer can then be added to the form and the tablet compressed. The blue colored portion with the abrasive inclusions made from an extruded polyol matrix can have the washboard surface formed from the bottom die of the tablet press. The piece size can be 1 gram total, with an equal sized top and bottom layer.

Example 2

Pressed Tablet

| First layer (white) | |
|---|---|
| Sorbitol | 98.11% |
| Intense sweeteners | 0.34% |
| Lemon/menthol flavor | 0.51% |
| Malic acid | 0.06% |
| Magnesium stearate | 0.98% |
| Total | 100.0 |

| Second layer (blue, fizzing) | |
|---|---|
| Sorbitol | 62.36% |
| Sodium bicarbonate | 19.96% |
| Malic acid | 16.21% |
| Intense sweeteners | 0.47% |
| Lemon/menthol flavor | 0.34% |
| Magnesium stearate | 0.62% |
| Blue color | 0.04% |
| Total | 100.0 |

For the first (white) layer, sorbitol, sweeteners, and acid were mixed for 5 minutes, flavor was added and mixed for 10 minutes, and then magnesium stearate was added and mixed for 2 minutes.

For the second (blue) layer, sorbitol, sweeteners, acid, bicarbonate, and color were mixed for 5 minutes, flavor was added and mixed for 10 minutes, and then magnesium stearate was added and mixed for 2 minutes.

Three parts of the white powder (about 0.66 grams) were placed in a die that included a mesh screen to form a rough surface, and tapped down. Two parts (about 0.44 grams) of blue powder were then poured into the die. The powders were compressed in the die, using about two metric tons of force. A two-layer white/blue tablet was formed. The blue layer was formed with an uneven surface conforming to the grids in the die. Those grids, along with crystals of the malic acid, provided an abrasive surface that scrubs the tongue.

In this example, the sodium bicarbonate and malic acid are stable while in their solid form. However, when the product is placed in the mouth, these two ingredients start to dissolve and interact with one another, producing an effervescent action on the tongue.

The abrasive inclusions can include encapsulated or entrapped flavors and colors. They can also be hard crystals of sugars or polyols, such as crystalline maltitol. The abrasive inclusions can also be other types of crystals, such as citric or malic acid, or other food acids that form hard crystals.

Examples 3A-H

A two layer pressed tablet was made according to the following formula.

| Layer 1 (bottom, scrubbing layer) | % |
|---|---|
| Sorbitol (Roquette Neosorb(TM)) | 65.94 |
| Palatinit Inclusions* | 32.97 |
| Magnesium Stearate | 0.49 |
| Peppermint Flavor | 0.49 |
| Aspartame | 0.07 |
| Acesulfame K | 0.02 |
| Cooling Agent (FEMA 4006) | 0.02 |
| | 100.00 |

*Palatinit (hydrogenated isomaltulose) particles with 0.30% food approved blue lake color sized to pass through a #20 sieve and be retained on a #40 sieve.

| Layer 2 (upper, smooth layer) | % |
|---|---|
| Sorbitol (Roquette Neosorb(TM)) | 98.91 |
| Magnesium Stearate | 0.49 |
| Peppermint Flavor | 0.49 |
| Aspartame | 0.07 |
| Acesulfame K | 0.02 |
| Cooling Agent (FEMA 4006) | 0.02 |
| | 100.00 |

Ingredients in the above formulas were dry blended together. A quantity of Layer 1 powder equal to 40% of the total piece weight was loaded into the die with lower punch (with tongue-cleaning features) inserted and compressed lightly by hand with the upper punch. The upper punch was removed and cleaned of loose powder. A quantity of Layer 2 powder equal to 60% of the total piece weight was loaded into the die/lower punch assembly on top of Layer 1 and compressed at 7000 pounds force to produce a bi-layer product having a lower, blue, tongue-cleaning layer with rough inclusions and a molded tongue-cleaning surface and an upper, white, generally smooth layer.

Pieces were formed using dies with upper and lower punches to produce shapes similar to some of those shown in the figures.

| | | Width/Thickness (in.) | Ratio |
|---|---|---|---|
| A. | FIGS. 17 and 18 | .458/.274 | 1.67 |
| B. | FIGS. 19 and 20 | .446/.252 | 1.77 |
| C. | FIGS. 33 and 34 | .407/.259 | 1.57 |
| D. | FIGS. 25 and 26 | .566/.254 | 2.23 |
| E. | FIGS. 23 and 24 | .462/.287 | 1.61 |
| F. | FIGS. 35 and 36 | .388/.256 | 1.52 |
| G. | FIGS. 27 and 28 | .559/.254 | 2.20 |
| H | FIGS. 15 and 16 | .578/.256 | 2.26 |

Informal testing indicated that the FIG. 27/28 product, the FIG. 25/26 product and the FIG. 15/16 product had the best resistance to "rolling" and were the easiest to manipulate with the tongue.

Example 4

The Example 3 Layer 1 and Layer 2 formulas were tableted as in Example 3 but on a Stokes BB2 3-layer, 24 station tablet press with dies and punches shaped to make the tablet shown in FIGS. 39/40, having a tablet weight of approximately 1.1 g, a width of 0.465 inches and a length of 0.625 inches. An initial compression pressure was set and a few tablets were made.

These were tested for hardness and the compression pressure adjusted up or down to produce tablets of the desired hardness, a target of 30 Kp. The force used to produce that hardness was 3.65 US tons, or 7300 pounds. This setting was dependent on the size and shape of the tablet produced. For the tablet of FIGS. 39/40, with a thickness of approximately 8.9 mm, a width of 0.465 inches and a length of 0.625 inches, the tablet has a maximum cross-sectional area of about 0.228 square inches. Thus, the 7300 pounds of force produced a pressure of about 32,000 psi.

Examples 5A-H

The Palatinit inclusions in the above Examples 3A-H are replaced with blue colored maltitol inclusions.

Examples 6A-H

The Palatinit inclusions in the above Examples 3A-H were replaced with blue colored mannitol inclusions (Roquette Pearlitol 500DC™)

Example 7

The confectionery tongue-cleaning product of Example 3 was repeated except that the Layer 1 (bottom scrubbing layer) was replaced with the following composition:

| Layer 1 (bottom, scrubbing layer) | % |
|---|---|
| Sorbitol (Roquette Neosorb(TM)) | 82.42 |
| Palatinit Inclusions* | 16.49 |
| Magnesium Stearate | 0.49 |
| Peppermint Flavor | 0.49 |
| Aspartame | 0.07 |
| Acesulfame K | 0.02 |
| Cooling Agent (FEMA 4006) | 0.02 |
| | 100.00 |

*same composition as in Ex. 3

The powder was used as before to prepare tablets using punches and die to produce the product illustrated in FIG. 23/24.

By having a hardness of between about 18 Kp and about 35 Kp, the tablets can stay in the mouth without dissolving for sufficiently long that they can be used to effectively scrub the tongue. This may be due to the surface shape, in which case the hardness preserves the surface abrasive features for long enough that the tongue can be scraped. If inclusions are included to provide the abrasive surface, then the hardness helps to keep the inclusions securely mounted in the tablet matrix, so that they do not become dislodged and thus loose their effectiveness. The desired hardness is in part achieved using the desired press force generating the desired pressure. The actual amount of force required will depend on the geometry of the tablet shape, and also somewhat on the materials used.

Example 8

Boiled Hard Candy

| First layer | |
|---|---|
| Isomalt | 99.14% |
| Lemon-mint flavor | 0.49% |
| Citric acid | 0.24% |
| Acesulfame/aspartame | 0.13% |
| Total | 100.0 |

| Second layer | |
|---|---|
| Isomalt | 98.62% |
| Abrasive inclusions | 0.51% |
| Lemon-mint flavor | 0.49% |
| Citric acid | 0.24% |
| Blue color | 0.01% |
| Acesulfame/aspartame | 0.13% |
| Total | 100.0 |

The isomalt is a syrup, boiled to about 1-3% moisture. As it cools, the flavor, acid, and sweeteners are added. When the second layer material is being made, the abrasive inclusions compound is also added as the low-moisture isomalt syrup cools. The second layer can be deposited into forms having a washboard surface on the bottom. This second layer will be deposited at a higher temperature to make it less viscous so that it conforms to the washboard surface of the mold. The top or first layer can then be added to the deposit form at a lower temperature with higher viscosity so as to keep the hard candy layers from mixing too much. The form with the blue layer will make a product that has a washboard appearance. The final piece size is 2 grams, equally divided between the layers.

Example 9

Boiled Hard Candy

| First layer | |
|---|---|
| Isomalt | 99.48% |
| Peppermint flavor | 0.40% |
| Sweeteners | 0.12% |
| Total | 100.0 |

| Second layer | |
|---|---|
| Isomalt | 74.76% |
| Abrasive inclusions | 24.71% |
| Peppermint flavor | 0.40% |
| Blue color | 0.01% |
| Sweeteners | 0.12% |
| Total | 100.0 |

Isomalt is dissolved in an aqueous solution and boiled to about 1-3% moisture. This material is used as the first ingredient in both layers. As the solution is cooled, the flavor and sweetener are added, and the abrasive inclusions, which are granular maltitol, are added to the syrup used to make the second layer. The second layer can be deposited into the deposit form with a washboard surface on the bottom of the deposit form. This second layer can be deposited at a higher temperature to make it less viscous. The top or first layer can then be added to the deposit form at a lower temperature with higher viscosity so as to keep the hard candy layer from mixing too much. The form with the blue layer will make a product that has a washboard appearance. The product is preferably a 2 gram piece, evenly divided between the layers.

The abrasive inclusions can include encapsulated or entrapped flavors and colors. They can also be hard crystals of sugars or polyols. In Example 3 the abrasive inclusions are crystalline maltitol. The abrasive inclusions can also be other types of crystals, such as citric or malic acid, or other food acids that form hard crystals.

The preferred embodiments of the invention have a smooth upper surface so that the roof of the mouth and gums are not irritated by the product while the abrasive surface is used to scrub the tongue. The preferred product has a small piece size so that it can be used discretely. The product can be used to scrub the tongue and other soft oral surfaces and remove odor causing bacteria while in public. By moving the specially formulated shape around in the mouth, the unique surface is designed to gently cleanse the mouth by lifting away the germs that cause bad breath in a way that the user can really feel. Clean and fresh breath, as well as other oral health benefits, are thus readily available. The products of the present invention provide an effective compliment to a daily oral care routine.

It should be appreciated that the products, processes and methods of the present invention are capable of being incorporated in the form of a variety of embodiments, only a few of which have been illustrated and described above. For example, other colors such as green may be used. The invention may thus be embodied in other forms without departing from its spirit or essential characteristics. It will be appreciated that the addition of some other ingredients, process steps, materials or components not specifically included will have an adverse impact on the present invention. The best mode of the invention may therefore exclude ingredients, process steps, materials or components other than those listed above for inclusion or use in the invention. However, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

The invention claimed is:

1. A hard confectionery product comprising:
   a) a first side and a second side generally opposite relative to said first side;
   b) the first side comprising a domed shape, non-abrasive surface; and
   c) the second side comprising an abrasive surface that is suitable for scrubbing the top surface of a tongue within an oral cavity wherein
      i) the abrasive surface is generally convex,
      ii) the abrasive surface comprises a formed, uneven surface,
      iii) the confectionery composition forming the uneven surface also contains abrasive particles, and
      iv) the abrasive surface comprises a plurality of protrusions protruding from the abrasive surface;
   d) wherein the product is generally elliptical in shape in plan view and has a size with no dimension greater than 25 mm and a product thickness of between about ⅛ and about ½ inch; and the smallest of the length and width of the second side is between about ¼ and about 1 inch; and
   e) wherein the product does not include a handle, the product does not include a combination of a soft confectionery with a hard confectionery, and the product comprises a pressed tablet and the confectionery includes one or more fruit flavors.

2. The hard confectionery product of claim 1 wherein the domed surface and abrasive surface are made from different compositions.

3. The product of claim 1 wherein the abrasive particles predominantly have particle sizes of between about 100 microns and about 2000 microns.

4. The product of claim 1 wherein the abrasive particles comprise a material selected from the group consisting of crystalline sugars, crystalline polyols, solid matrices of carbohydrates, solid matrices of polyols, extruded carbohydrates, extruded polyols, granular food acids, granular inorganic salts and mixtures thereof.

5. The product of claim 1 wherein the abrasive particles are of a different color than the material in which they are contained.

6. The product of claim 1 wherein the abrasive particles also carry a flavor.

7. The product of claim 1 which is sugarless.

8. The product of claim 1 having a piece weight of between about 1 and about 2 grams.

9. The product of claim 1 further comprising one or more anti-microbial agents.

10. The product of claim 1 wherein the product comprises one or more physiological cooling agents.

11. The product of claim 1 wherein the product comprises one or more breath freshening agents.

12. The product of claim 1 wherein the product comprises one or more breath freshening and mouth odor masking flavors.

13. A pressed tablet comprising:
   a) two distinct layers, a first layer comprising a first hard confectionery composition and a second layer comprising a second hard confectionery composition;
   b) the first composition formed so as to have a domed shape, non-abrasive surface;
   c) the second composition being different than said first composition and the second composition having formed thereon an uneven, abrasive surface generally opposite said non-abrasive surface and that is suitable for scrubbing the top surface of a tongue within an oral cavity, wherein
      i) the abrasive surface is generally convex,
      ii) the second composition contains abrasive particles, and
      iii) the abrasive surface comprises a plurality of protrusions protruding from the abrasive surface;
   d) wherein the product is generally elliptical in shape in plan view and has a size with no dimension greater than 25 mm and a product thickness of between about ⅛ and about ½ inch; and the smallest of the length and width of the product is between about ¼ and about 1 inch; and
   e) wherein the product does not include a handle, the product does not include a combination of a soft confectionery with a hard confectionery, and the confectionery includes one or more fruit flavors.

14. The pressed tablet of claim 13 wherein the first and second compositions are different in color from one another.

15. The pressed tablet of claim 14 wherein the first composition is a generally white color.

16. The pressed tablet of claim 13 wherein the distinct layers form an interface generally parallel to the abrasive surface.

17. The pressed tablet of claim 13 wherein the first and second compositions both comprise one or more materials selected from the group consisting of sugars and sugar alcohols.

18. A hard confectionery product comprising:
   a) a first side and a second side generally opposite relative to said first side;
   b) the first side comprising a smooth, domed shape surface; and
   c) the second side comprising a formed, generally convex, uneven, abrasive surface that is suitable for scrubbing the top surface of a tongue within an oral cavity, the second side being made of a hard confectionery material comprising abrasive particles, the abrasive surface comprising a plurality of protrusions protruding from the abrasive surface;
   d) wherein the product has a size with no dimension greater than 25 mm and a product thickness of between about ⅛ and about ½ inch; and the smallest of the length and width of the product is between about ¼ and about 1 inch; and
   e) wherein the product does not include a handle, the product does not include a combination of a soft confectionery with a hard confectionery, and the product comprises a pressed tablet and the confectionery includes one or more fruit flavors.

19. The product of claim 18 wherein the pressed tablet has a hardness of between about 18 Kp and about 35 Kp.

20. The product of claim 18 wherein the formed surface is molded using a compression die.

21. The product of claim 1 wherein the plurality of protrusions protruding from the abrasive surface comprise a plurality of individual bumps.

22. The pressed tablet of claim 13 wherein the plurality of protrusions protruding from the abrasive surface comprise a plurality of individual bumps.

23. The product of claim 18 wherein the plurality of protrusions protruding from the abrasive surface comprise a plurality of individual bumps.

24. The hard confectionery product of claim 1 wherein the product is oval in shape in plan view.

* * * * *